(12) United States Patent
Hildreth et al.

(10) Patent No.: US 9,050,460 B2
(45) Date of Patent: Jun. 9, 2015

(54) SYSTEM AND METHOD FOR RADIATION BEAM MEASUREMENT NORMALIZATION

(71) Applicant: SUN NUCLEAR CORPORATION, Melbourne, FL (US)

(72) Inventors: Jeffrey L. Hildreth, Melbourne, FL (US); Thomas Simon, Rockledge, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 0 days.

(21) Appl. No.: 14/081,416

(22) Filed: Nov. 15, 2013

(65) Prior Publication Data

US 2014/0073834 A1 Mar. 13, 2014

Related U.S. Application Data

(63) Continuation-in-part of application No. 13/875,840, filed on May 2, 2013, now abandoned.

(60) Provisional application No. 61/641,511, filed on May 2, 2012.

(51) Int. Cl.
  *A61B 6/00* (2006.01)
  *A61N 5/00* (2006.01)
  *A61N 5/10* (2006.01)

(52) U.S. Cl.
  CPC ....... *A61N 5/1048* (2013.01); *A61N 2005/1054* (2013.01); *A61N 5/1075* (2013.01)

(58) Field of Classification Search
  CPC ........ A61B 6/032; A61B 6/583; A61B 6/482; A61B 5/1031; A61B 5/1048; A61B 5/1075; A61B 5/1049; A61B 5/00; G01T 1/29; G06T 7/0034; G21G 1/12
  USPC ........... 250/492.3, 252.1, 336.1, 391; 378/65, 378/19, 7, 82
  See application file for complete search history.

(56) References Cited

U.S. PATENT DOCUMENTS

| 5,099,505 | A | * | 3/1992 | Seppi et al. | 378/65 |
|---|---|---|---|---|---|
| 5,627,367 | A | | 5/1997 | Sofield | |
| 6,535,756 | B1 | * | 3/2003 | Simon et al. | 600/424 |
| 6,990,368 | B2 | * | 1/2006 | Simon et al. | 600/425 |
| 7,453,976 | B1 | * | 11/2008 | Yin | 378/9 |
| 8,218,718 | B1 | * | 7/2012 | Van Herk et al. | 378/7 |
| 8,541,756 | B1 | * | 9/2013 | Treas | 250/398 |
| 8,874,385 | B2 | * | 10/2014 | Takayanagi et al. | 702/40 |
| 8,927,921 | B1 | * | 1/2015 | Nelms et al. | 250/252.1 |
| 2008/0118137 | A1 | * | 5/2008 | Chen et al. | 382/131 |
| 2011/0022360 | A1 | | 1/2011 | Simon et al. | |
| 2011/0096906 | A1 | * | 4/2011 | Langeveld | 378/82 |

(Continued)

*Primary Examiner* — David A Vanore
(74) *Attorney, Agent, or Firm* — Mintz Levin Cohn Ferris Glovsky and Popeo, P.C.

(57) ABSTRACT

A radiotherapy system includes a radiotherapy device, such as a LINAC, operable to direct a radiation beam from a head thereof during operation, a field detector positioned to be within the radiation beam during operation of the radiotherapy device and operable to generate a beam measurement signal, a reference detector positioned to be outside of the radiation beam during operation of the radiotherapy device and operable to generate a reference signal, and at least one computer in signal communication with the field detector and the reference detector and configured with software to normalize the beam measurement signal based on the reference signal and to output a normalized beam measurement.

16 Claims, 3 Drawing Sheets

(56) References Cited

U.S. PATENT DOCUMENTS

| | | | |
|---|---|---|---|
| 2012/0014618 A1* | 1/2012 | Sun et al. | 382/286 |
| 2012/0025105 A1* | 2/2012 | Brown et al. | 250/492.3 |
| 2012/0326057 A1* | 12/2012 | Remeijer et al. | 250/492.1 |
| 2013/0048883 A1* | 2/2013 | Simon et al. | 250/492.3 |
| 2014/0073834 A1* | 3/2014 | Hildreth et al. | 600/1 |
| 2014/0263990 A1* | 9/2014 | Kawrykow et al. | 250/252.1 |

* cited by examiner

SYSTEM AND METHOD FOR RADIATION BEAM MEASUREMENT NORMALIZATION

CROSS-REFERENCE TO RELATED APPLICATIONS

This application is a continuation-in-part of U.S. Non-Provisional Patent Application Ser. No. 13/875,840, filed on May 2, 2013, which claims the benefit of U.S. Provisional Application Ser. No. 61/641,511, filed on May 2, 2012, the contents of which applications are herein incorporated by reference in their entirety.

FIELD OF THE INVENTION

The present invention relates to radiotherapy systems, and more particularly, to systems and methods for normalizing radiation beam measurements to compensate for variations in radiation output.

BACKGROUND OF THE INVENTION

Linear accelerator (LINAC) relative dosimetry (beam scanning) involves acquiring a measurement of the radiation beam with a field detector and typically a reference detector. The measurement is acquired as two parameters are varied: the field detector's position and time. Using the measured signal from the field detector, a plot of the LINAC's radiation beam intensity versus position within that beam is possible, with an example shown in FIG. 1.

Beam scanning often requires normalizing the measured signal from a field detector by the measured signal from a reference detector. This occurs because the output of the LINAC may change with time, sometimes abruptly. For example, an increase in the LINAC radiation dose rate during a scan results in an increase in the field detector's measured signal. If only a field detector is used, the beam scan will show a change in the beam intensity at that point in space that corresponds to when the LINAC's radiation output changed. This irregularity in the measurement is not indicative of the actual relative dose intensity of the radiation beam. In FIG. 2, a repeat of the scan from FIG. 1 is shown, but in which the LINAC's dose rate changed (increased) during the scan. This change caused the marked change in the amplitude of the beam's relative dose intensity.

Small changes in LINAC dose rate do not affect the radiation therapy treatment. The change in the dose rate effectively changes the amount of time in which the radiation dose is delivered, which is not important to the treatment parameters being measured. The more important parameter during beam scanning is the relative dose intensity of the beam. Using only a field detector may misrepresent this characteristic of the LINAC's radiation beam, as in FIG. 2.

To correct for changes in a LINAC's dose rate, a reference detector is used to normalize dose rate changes. For example, referring to FIG. 3, a radiotherapy system 110 includes a reference detector 120 that is stationary and located in the radiation beam 124. Considering the above example, when the LINAC 112 dose rate increased, it increases the measured signal of the field detector 116, which would otherwise misrepresent the relative dose intensity of the radiation beam 124 (as in FIG. 2). However, the increase in the field detector's measured signal should be matched by a proportional increase in the reference detector's measured signal. A ratio of the field detector's measured signal to the reference detector's measured signal corrects for the changed dose rate that occurred during a scan. The measurement would then match that of FIG. 1, correctly representing the beam's relative dose intensity. While this approach to beam measurement normalization is useful, further improvements are possible.

SUMMARY OF THE INVENTION

In view of the foregoing, it is an object of the present invention to provide radiotherapy systems with improved systems and methods for radiation beam measurement normalization. According to an embodiment of the present invention, a radiotherapy system includes a radiotherapy device, such as a LINAC, operable to direct a radiation beam from a head thereof during operation, a field detector positioned to be within the radiation beam during operation of the radiotherapy device and operable to generate a beam measurement signal, a reference detector positioned to be outside of the radiation beam during operation of the radiotherapy device and operable to generate a reference signal, and at least one computer in signal communication with the field detector and the reference detector and configured with software to normalize the beam measurement signal based on the reference signal and to output a normalized beam measurement.

According to a method aspect, a computer-based method for normalizing a radiation beam measurement includes using at least one computer configured with software to receive a beam measurement signal from a field detector positioned within the radiation beam, receive a reference signal from a reference detector positioned outside of the radiation beam, normalize the beam measurement signal based on the reference signal, and output a normalized beam measurement.

These and other objects, aspects and advantages of the present invention will be better appreciated in view of the drawings and following detailed description of preferred embodiments.

DETAILED DESCRIPTION OF PREFERRED EMBODIMENTS

Figure 1:
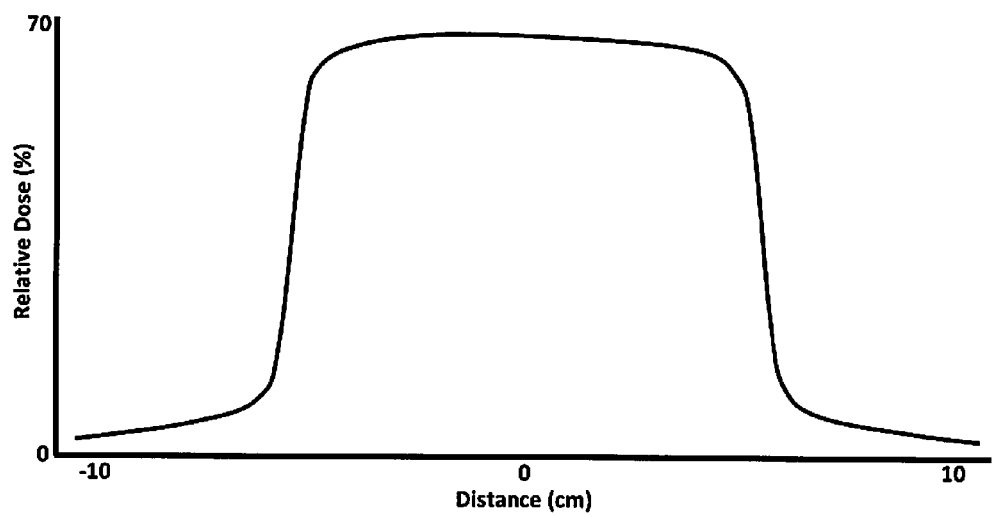
FIG. 1 is graph of a normalized beam measurement.
Figure 2:
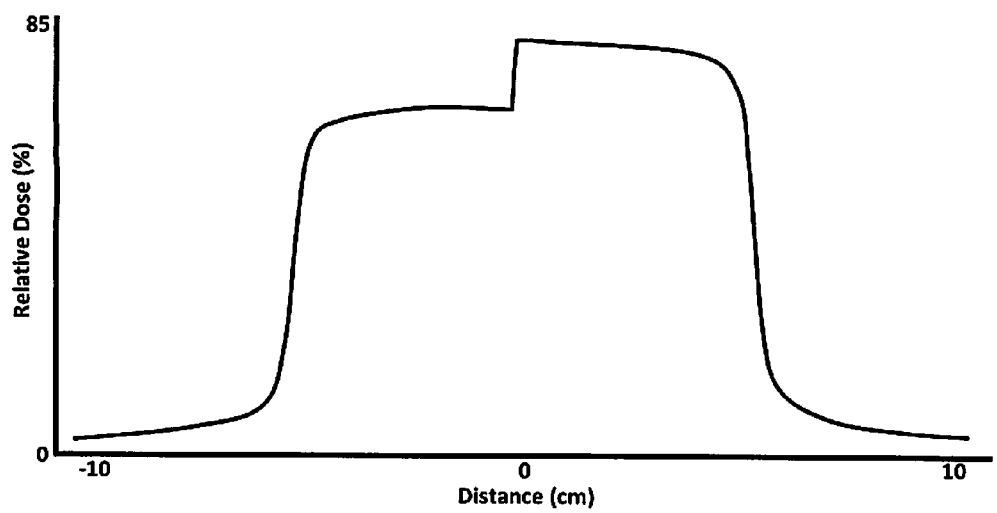
FIG. 2 is a graph of a non-normalized beam measurement.
Figure 3:
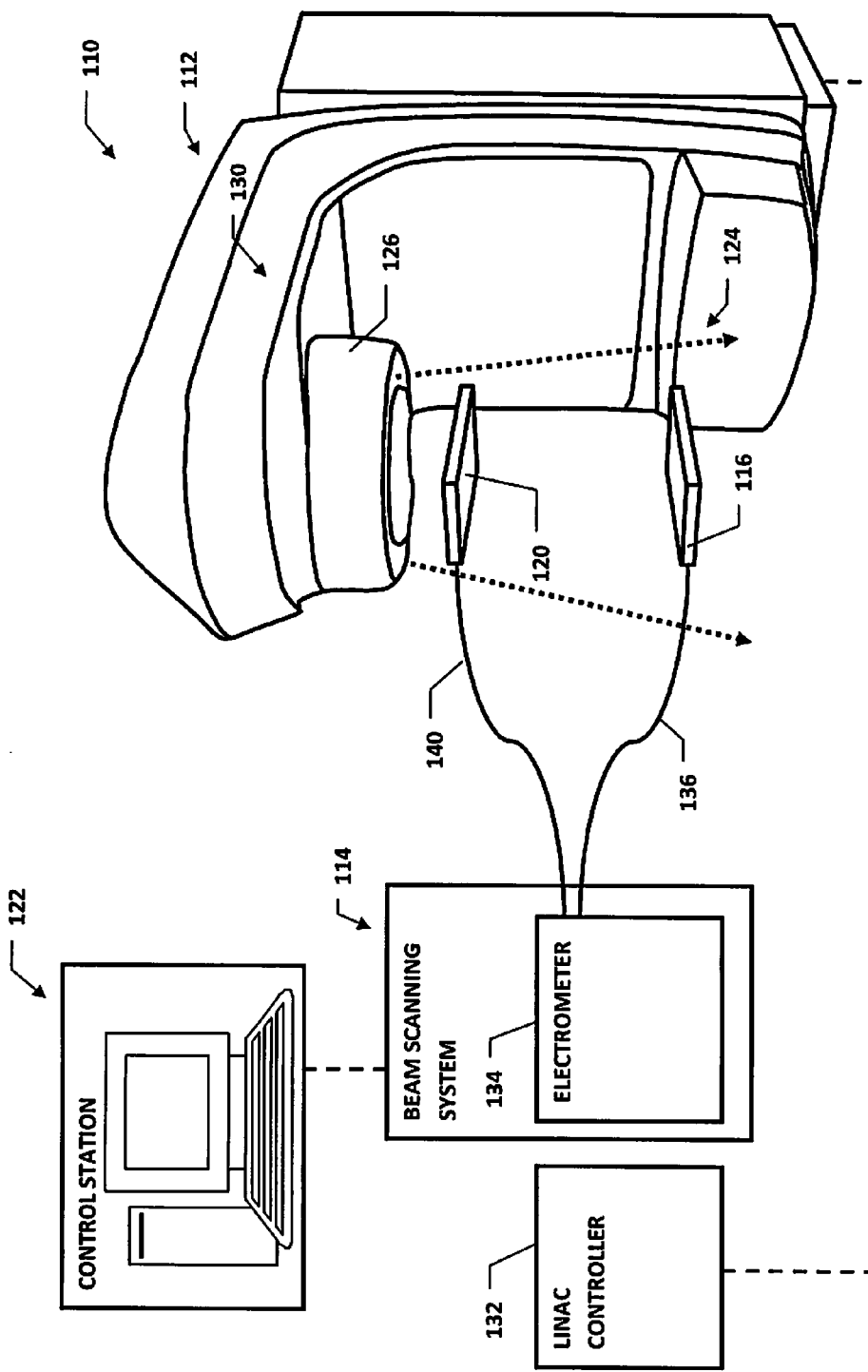
FIG. 3 is schematic view of a radiotherapy system configured for beam measurement normalization.
Figure 4:
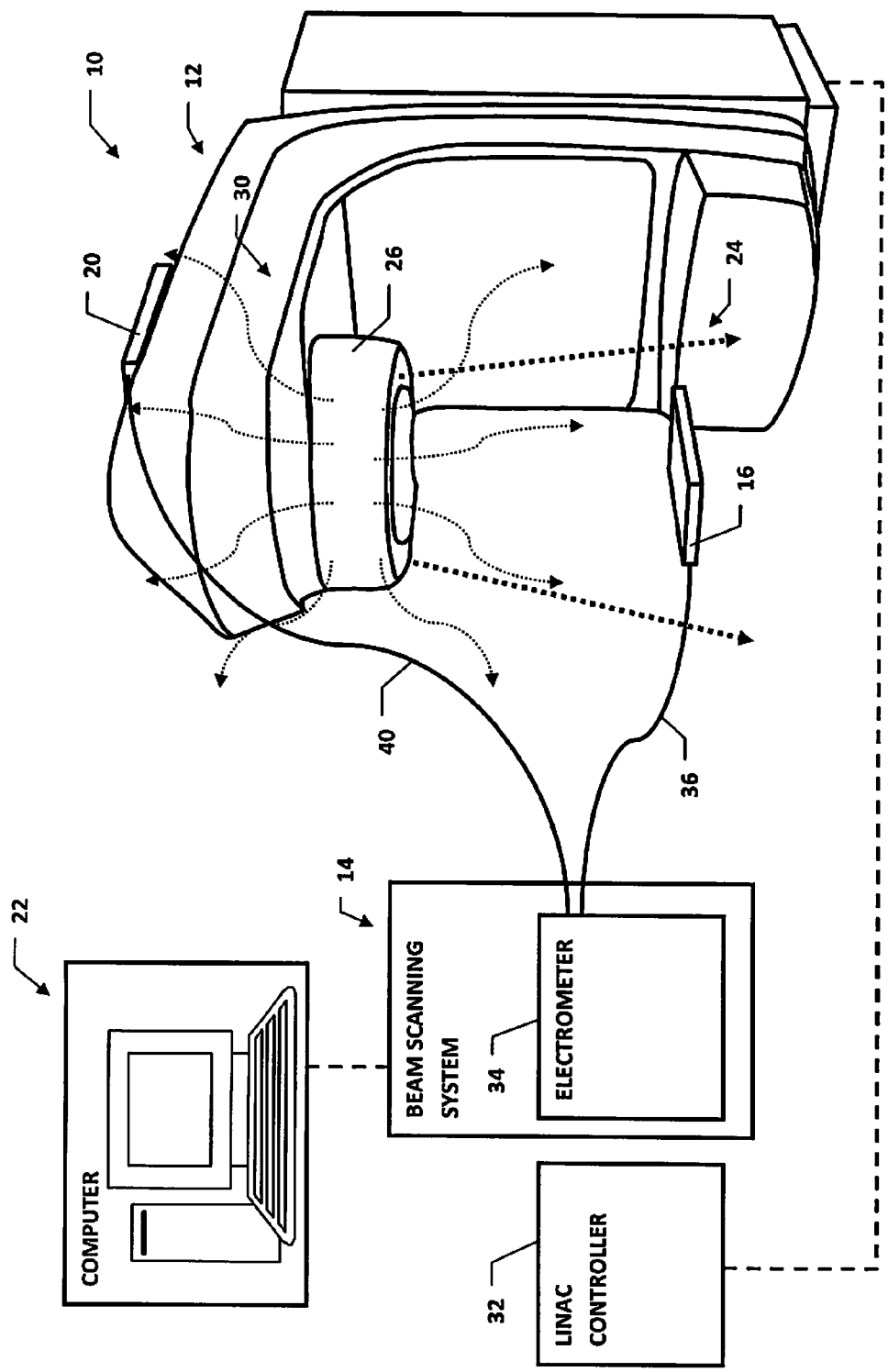
FIG. 4 is a schematic view of a radiotherapy system configured for beam measurement normalization, according to an embodiment of the present invention.

Referring to FIG. 4, according to an embodiment of the present invention, a radiotherapy system 10 includes a radiotherapy device 12, a beam scanning system 14 receiving signals from field and reference detectors 16, 20, and a computer 22 in signal communication with the detectors 16, 20 via the beam scanning system 14. The radiotherapy device 12 is operable to direct a radiation beam 24 from a head 26 thereof, the operation also producing head scatter 30. The field detector 16 is arranged so as to be in the radiation beam 24 and operable to generate a beam measurement signal, while the reference detector 20 is positioned to be outside of the radiation beam and operable to generate a reference signal based on the head scatter 30. The computer 22 is configured with software to normalize the beam measurement signal based on the reference signal and to output a normalized beam measurement.

The radiotherapy device 12 is advantageously a linear accelerator (LINAC) used in connection with beam scanning during operation (i.e., measuring the relative dose intensity). Generation and movement of the radiation beam and rotation of the head 26 are performed by a LINAC controller 32 capable of sending and receiving control signals to the LINAC 12 to effect device operation.

The beam scanning system 14 includes an electrometer 34 connected to the field and reference detectors 16, 20 by respective cables 36, 40. The acquired electrical charge of the detectors 16, 20 is thereby supplied the electrometer 34 for measurement, with the measured values being output to the computer 22. If it is necessary to provide a polarizing voltage to the field and reference detectors 16, 20, the polarizing voltage is provided via their respective cables 36, 40 and the electrometer 34.

The field and reference detectors 16, 20 are both configured to detect ionizing radiation which, as indicated above, will alter the acquired charge of the detectors. The field detector 16 is placed where it will be in the radiation beam 24 emitted by the LINAC 12 during operation. The reference detector 20 is placed at location that will be outside of the radiation beam 24 during operation, but still exposed to head scatter 30; for instance, on top of the head 26. In a LINAC, the head scatter is produced by interactions between the LINAC-generated beam and components of the LINAC head. Notably, the depicted beam 24 and head scatter 30 are provided for illustrative purposes, and not intended to reflect actual geometries)

As used herein, the term "computer" (e.g., the computer 22) is used to broadly indicate at least one hardware processor capable of executing program instructions, machine-readable memory media for storing such instructions and related data used and/or generated during the operation thereof. Typically, a computer will also include one or more input/output devices, such as video displays, keyboards, pointing devices and the like. A "computer" can encompass multiple, physically discrete and separately housed processors, memory media and the like that are in signal communication (for instance, via a network) to perform the enumerated functions. Additionally, the computer 22 can be structurally and/or functionally integrated with some or all of the beam scanning system 14 and/or LINAC controller 32.

The computer 22 is configured with software to output a normalized beam measurement based on the beam measurement signal and the reference signal. In particular, the software directs the calculation of the ratio of the beam measurement signal from the field detector and the reference signal from the reference detector. This effectively normalizes the beam measurement since changes in dose rate will affect the numerator and the denominator in the same proportion. This is because the dose rate of the beam and the heat scatter rate are linearly proportional. Minor changes in beam shape, on the other hand, will not affect the head scatter rate.

The present invention can offer several advantages over normalization that requires locating the reference detector within the radiation beam. For example, accurate beam normalization is still possible even where the radiation beam size too small to accommodate both a field detector and a reference detector. Also, it is not necessary to reposition the reference detector as the beam size changes. The reference detector can be securely mounted in a fixed location, making unintentional movement of the reference detector less likely. Additionally, as mentioned above, the reference detector will not be sensitive to fluctuations in beam shape during scanning, which might otherwise affect the reference detector independently of the field detector.

The above described embodiments are presented for illustrative and exemplary purposes; the present invention is not necessarily limited thereto. Rather, those skilled in the art will appreciate that various modifications, as well as adaptations to particular circumstances, will fall within the scope of the invention herein shown and described and of the claims appended hereto.

What is claimed is:

1. A radiotherapy system comprising:
a radiotherapy device operable to direct a radiation beam from a head thereof during operation;
a field detector positioned to be within the radiation beam during operation of the radiotherapy device and operable to generate a beam measurement signal;
a reference detector positioned to be outside of the radiation beam during operation of the radiotherapy device and operable to generate a reference signal; and
at least one computer in signal communication with the field detector and the reference detector and configured with software to normalize the beam measurement signal based on the reference signal and to output a normalized beam measurement.

2. The radiotherapy system of claim 1, wherein the radiotherapy device is a linear accelerator (LINAC).

3. The radiotherapy system of claim 2, wherein the normalized beam measurement output is a measurement of a relative intensity of the radiation beam versus position.

4. The radiotherapy system of claim 2, wherein the reference detector is positioned to measure head scatter from the LINAC.

5. The radiotherapy system of claim 1, wherein the radiotherapy device includes a movable gantry that carries the head, and the reference detector is carried on the movable gantry so as to move therewith.

6. The radiotherapy system of claim 5, wherein the head directs the radiation beam away from a first side of the movable gantry and the reference detector is carried on a second side of the movable gantry opposite the first side.

7. The radiotherapy system of claim 1, further comprising at least one electrometer configured to measure the beam measurement and reference signals and output respective measured beam measurement and reference signals to the at least one computer.

8. The radiotherapy system of claim 7, wherein the electrometer is connected to the field detector and the reference detector by respective cables.

9. A computer-based method for normalizing a radiation beam measurement, the method comprising using at least one computer configured with software to:
receive a beam measurement signal from a field detector positioned within the radiation beam;
receive a reference signal from a reference detector positioned outside of the radiation beam;
normalize the beam measurement signal based on the reference signal; and
output a normalized beam measurement.

10. The computer-based method of claim 9, further comprising positioning the reference detector to receive head scatter from a radiotherapy device.

11. The computer-based method of claim 10, wherein the radiotherapy device is a linear accelerator (LINAC).

12. The computer-based method of claim 11, wherein positioning the reference detector includes positioning the reference detector on an opposite side of a gantry carrying a radiation beam-emitting head of the LINAC.

13. The computer-based method of claim 11, wherein the normalized beam measurement is a measurement of a relative intensity of the radiation beam versus position.

14. The computer-based method of claim 10, further comprising connecting the reference detector to an electrometer with a cable.

15. A system for normalizing a radiation beam measurement, the system comprising at least one computer configured with software to:
- receive a beam measurement signal from a field detector positioned within the radiation beam;
- receive a reference signal from a reference detector positioned outside of the radiation beam;
- normalize the beam measurement signal based on the reference signal; and
- output a normalized beam measurement.

16. The system of claim 15, wherein the normalized beam measurement is a measurement of a relative intensity of the radiation beam versus position.

* * * * *